United States Patent [19]

Wardlaw

[11] 4,266,544
[45] * May 12, 1981

[54] HYPODERMIC SYRINGE

[76] Inventor: Stephen C. Wardlaw, 128 Sunset Hill Dr., Branford, Conn. 06405

[*] Notice: The portion of the term of this patent subsequent to Feb. 19, 1997, has been disclaimed.

[21] Appl. No.: 93,134

[22] Filed: Nov. 9, 1979

[51] Int. Cl.³ .............................................. A61M 5/00
[52] U.S. Cl. ................................. 128/218 N; 128/221
[58] Field of Search .......... 128/218 R, 218 N, 218 F, 128/215, 216, 213, 221

[56] References Cited

U.S. PATENT DOCUMENTS

| 3,605,744 | 9/1971 | Dwyer | 128/218 F |
| 3,890,971 | 6/1975 | Leeson et al. | 128/218 R |
| 3,893,608 | 7/1975 | Koenig | 128/218 R |
| 4,188,950 | 2/1980 | Wardlaw | 128/218 F |

Primary Examiner—John D. Yasko
Attorney, Agent, or Firm—William W. Jones

[57] ABSTRACT

A hypodermic syringe which has provisions for preventing more than one use thereof and rendering the needle inoperative and harmless. A device is mounted on the syringe which, after administering an injection, is manipulated to bend the needle portion of the syringe and concurrently retract the needle from its normally projecting position whereby the needle cannot accidentally cause injury to anyone.

8 Claims, 6 Drawing Figures

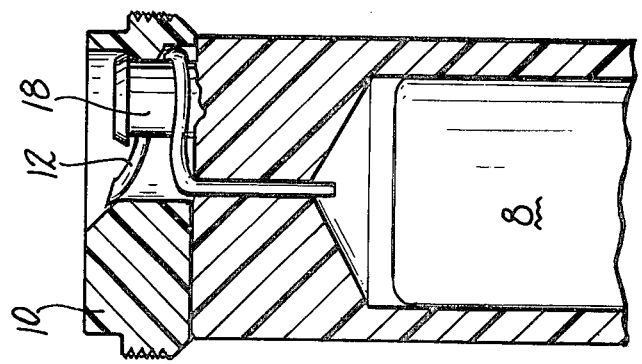
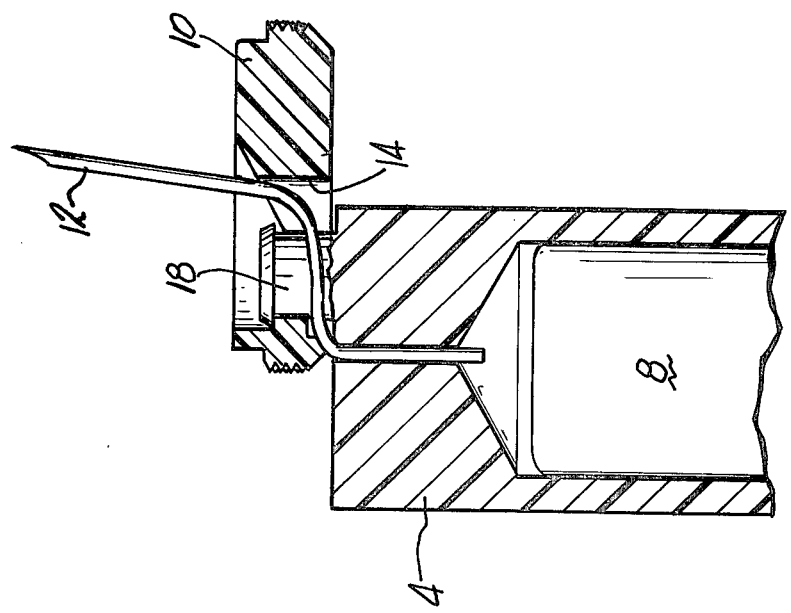
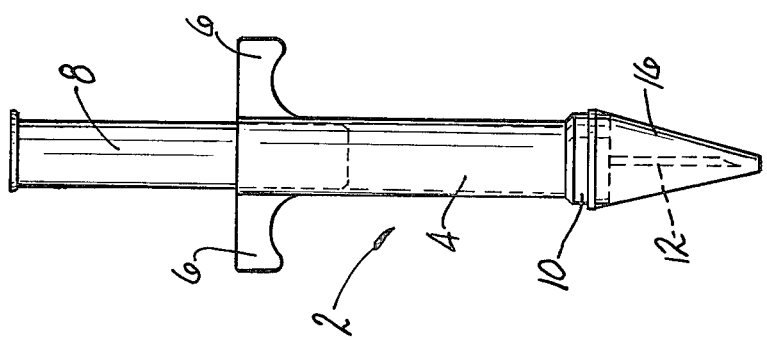

HYPODERMIC SYRINGE

This invention relates to an improved hypodermic syringe of the type which is disposable after a single use. The syringe of this invention cannot be used after the initial use thereof, and, after such initial use, the needle is bent and retracted so that it cannot cause accidental injury to anyone.

The vast majority of syringes presently in use are designed to be used only once and then discarded. This type of syringe is typically constructed from injection molded plastic fitted with a needle or cannula, and then sterilized and packaged so as to maintain its sterility. When used, the package is opened, the syringe removed and filled with the drug or medication to be administered, and then discarded after such usage.

Such syringes are generally provided with a removable cap which covers the needle before use so as to prevent accidental injury. The cap is removed before the medication is drawn into the syringe. If not misplaced or dicarded, the cap may be re-positioned on the syringe after use and before the syringe is discarded. The cap may, however, be easily removed again from the discarded syringe, thereby permitting illicit reuse of the syringe. Of course, if the cap is misplaced or discarded prior to administering the injection, the syringe must be discarded with an exposed needle.

The problem of potential injury and illicit reuse of disposable syringes has been recognized and has been dealt with in a number of different ways by the prior art. One practice in hospitals is to utilize a special tool with which the needle is clipped off of the syringe and then discarded. Thus, the syringe is rendered inoperative and harmless. This technique, however, requires the use of an accessory tool which must be carried about by the hospital staff. Also, the discarded needles can present an injury problem. To counter this problem, it has been proposed that the severed needles should be ground up to render them harmless. This, however, presents a potential health problem since the needles can be infected with hepatitis germs, or the like.

Another procedure for rendering the needle of a syringe inoperative and harmless is disclosed in U.S. Pat. No. 3,893,608, issued July 8, 1975 to E. A. Koenig. The Koenig construction includes a rod member formed as a part of the syringe, the rod member being detachable from the rest of the syringe after an injection is administered, and the rod including an offset chamber into which the needle is inserted. The offset in the chamber bends the needle and the rod member is frictionally telescoped onto the syringe over the needle so as to cover the needle. Thus, the needle is covered over and bent.

I have devised an improved syringe having provisions for bending and retracting a needle after an injection has been administered. The syringe, in its preferred embodiment, is formed with a rotatable member attached to its needle-bearing end. The member has a passage through it through which the needle extends. The member is rotatable about an axis which is offset from the needle passage. Rotation of the member is about a post formed on the remainder of the syringe. As the member is rotated about the post, the edge of the member passage engages the needle and pulls the free end of the needle back beneath the member and the needle is wrapped around the post. Preferably, one complete 360° revolution of the member passage causes the needle to be completely retracted between the member and the remainder of the syringe and, at the same time, be wrapped around the post. Thus, the needle is retracted and at the same time functionally destroyed. The syringe is thus rendered inoperable and incapable or accidentally causing injury.

It is, therefore, an object of this invention to provide a hypodermic syringe which can be disabled and rendered harmless after a single usage.

It is a further object of this invention to provide a syringe of the character described wherein the needle is retracted from its normal projecting position so as to render the needle incapable of accidentally harming anyone after the syringe has been used and discarded.

It is yet another object of this invention to provide a syringe of the character described wherein the needle is bent during retraction so as to prevent the syringe from being used more than once.

These and other objects and advantages of the invention will become more readily apparent from the following detailed description of several preferred embodiments thereof when taken in conjunction with the accompanying drawings, in which:

FIG. 1 is a side elevational view of a preferred embodiment of a syringe embodying the invention;

FIG. 4 is an axial sectional view similar to FIG. 3 but showing the mode of operation of the needle bender-retractor after the latter has been rotated through a 180° angle;

FIG. 5 is an axial sectional view similar to FIGS. 3 and 4, but showing the syringe after the needle has been completely retracted and rendered unusable.

Figure 2:
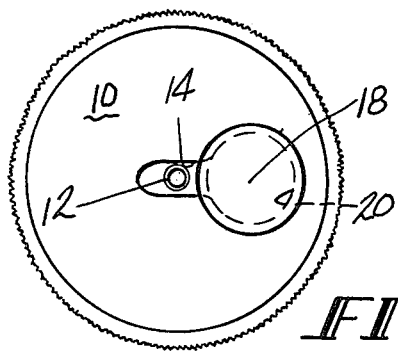
FIG. 2 is an end elevational view of the needle-bearing end of the syringe of FIG. 1 with the protective cap removed.

Referring now to the drawings, FIG. 1 discloses a modified form of a generally conventional syringe, denoted generally by the numeral 2, which syringe 2 includes a preferred embodiment of the needle retracting and bending device formed in accordance with this invention. The syringe 2 includes a hollow tubular portion 4 into and from which the medication is drawn and administered. Lateral finger grips 6 are disposed on either side of the tubular portion 4 to facilitate manual operation of the syringe. A piston member 8 is slidably mounted in the tubular portion 4 for filling and dispensing the medication in a conventional manner. A disk 10 is rotatably mounted on the end of the tubular body 4 remote from the piston 8, and a hypodermic needle 12 is secured to the end of the tubular portion 4, projecting therefrom through a passage 14 (see FIG. 3) in the disk 10. The protective sheath 16 is releasably pressed onto the disk 10 to protect the needle 12 during storage prior to use of the syringe 2.

Figure 3:
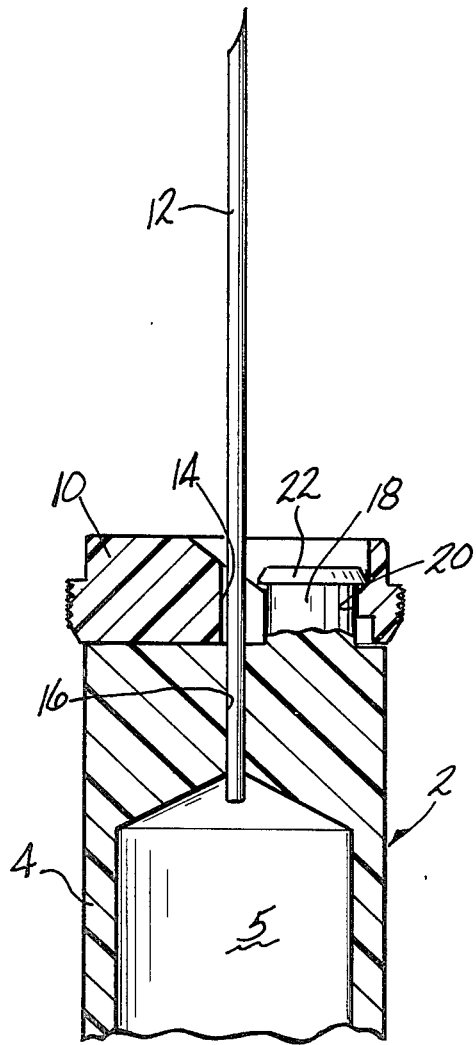
FIG. 3 is an axial sectional view of the needle-bearing end portion of the syringe of FIG. 1.

Referring now to FIGS. 2 and 3, the specific structure of the needle-bearing end of the syringe 2 is shown. It will be noted that the needle 12 extends through a passage 14 in the end wall of the tubular portion 4 so as to communicate with the medication chamber 5 which is within the tubular portion 4. Formed on the needle-bearing end wall of the tubular portion 4, and projecting therefrom, is a lug 18. It will be seen from FIGS. 2 and 3 that the passage 14 through the disk 10 communicates with a larger passage 20 through which the lug 18 extends. A circumferential rib 22 formed on the lug 18 engages the edge of the passage 20 so as to retain the disk 10 on the end of the tubular portion 4. From FIG. 2, it will be apparent that the sides of the passage 14 are closely proximate to the needle 12. It will be noted that the axis of the lug 18 is laterally offset from the axis of the needle 12, and that the axis of the lug 18 provides an axis about which the disk 10 may be rotated, as shown in FIG. 4.

Referring now to FIGS. 4 and 5, the mode of operation of the device for rendering the needle 12 incapable of hurting anyone or being reused is disclosed. Once the injection has been administered by depressing the piston 8, the disk 10 is rotated about the lug 18 through one or more 360° revolutions. This rotation of the disk 10 causes the passage 14 to swing about the lug 18 whereby the side wall of the passage 14 is moved against the needle 12. Since the end of the needle 12 is secured to the end of the tubular portion 4 of the syringe 2, movement of the passage sidewall against the needle 12 causes the needle 12 to be drawn back into the passage 14 and wrapped about the lug 18, as shown in FIG. 4. Continued rotation of the disk 10 about the lug 18 ultimately results in complete withdrawal of the needle 12 with the latter being completely wrapped about the lug 18 and overlain by the disk 10. Thus, the simple manual operation of the disk 10 after administering the injection simultaneously renders the syringe harmless and non-reusable.

Figure 6:
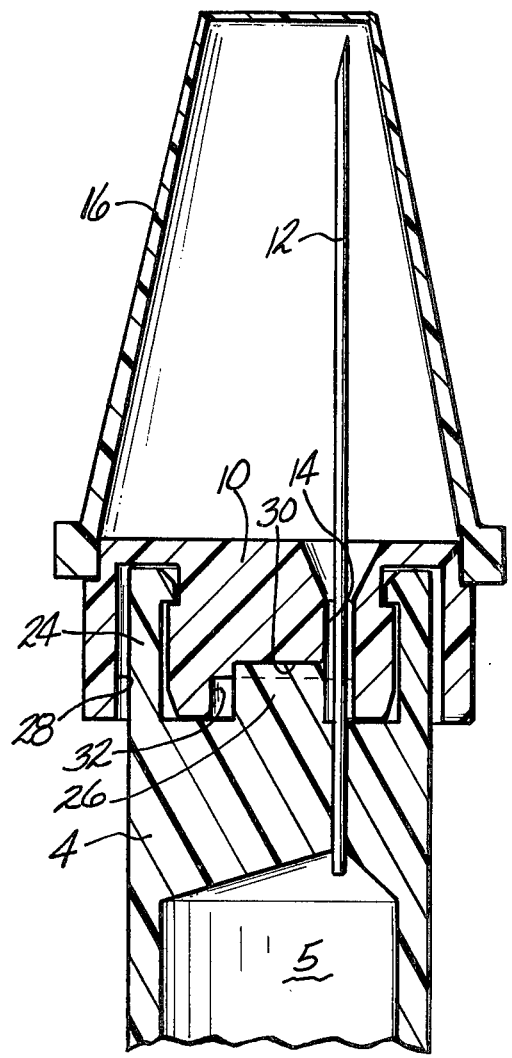
FIG. 6 is an axial sectional view similar to FIG. 3 but showing an alternative construction of the needle retracting and bending member.

Referring now to FIG. 6, an alternative embodiment of a syringe formed in accordance with this invention is disclosed. The syringe of FIG. 6 includes a tubular portion 4 having a medicament chamber 5 and a needle 12. A rotatable disk 10 is mounted on the needle-bearing end of the syringe and a protective cap 16 is releasably mounted on the disk 10 to cover the needle 12 prior to use. A forwardly projecting annular flange 24 is formed on the tubular portion 4, as is a central, forwardly projecting lug 26. An annular recess 28 is formed on the disk 10 for reception of the flange 24, and a blind hole 30 is formed in the disk 10 for reception of the lug 26. The blind hole 30 has an enlarged counter bore 32 which is radially spaced from the side wall of the lug 26 to form a covered chamber into which a portion of the deformed needle will be drawn. A passage 14 extends through the disk 10, the needle 12 projecting through the passage 14. It will be noted that the annular flange 24 and the lug 26 are coaxial while the passage 14 is off center from the common axis of the flange 24 and lug 26. Thus, when the disk 10 is rotated, the sides of the passage 14 move against the needle 12 and, since the inner end of the needle 12 is fixed, bend the needle 12 around the lug 26 and pull the needle 12 back into the counter bore 32. The needle 12 is thus bent and retracted whereby the syringe is rendered non-reusable and incapable of harming anyone.

It will be readily appreciated that this invention is operable to modify an otherwise conventional syringe so as to effectively limit the use of the syringe to a single use, and also to render the syringe, after use, incapable of harming anyone. A simple construction is utilized for concurrently bending and retracting the needle with a simple manual manipulation of the syringe.

Since many changes and variations of the disclosed embodiments of the invention may be made without departing from the inventive concept, it is not intended to limit the invention otherwise than as required by the appended claims.

What is claimed is:

1. An improved disposable syringe adapted to be used but once, said syringe comprising:
    (a) a hollow tubular portion for containing a medicament dose, and a hypodermic needle secured to one end of said tubular portion and projecting therefrom;
    (b) means in said hollow tubular portion for pumping a dose of medicament therefrom through said needle; and
    (c) retracting means movably mounted on said housing, said retracting means being operable to engage said needle and bend the latter to pull said needle from its projecting position to a safe position wherein said needle is covered over by a portion of said syringe.

2. An improved disposable syringe adapted to be used but once, said syringe comprising:
    (a) a hollow tubular portion for a medicament dose, and a hypodermic needle disposed on one end of said tubular portion projecting therefrom;
    (b) means in said housing for pumping a dose of medicament therefrom through said needle; and
    (c) a retracting member movably mounted on said housing, said retracting member being disposed on said housing in a position wherein said needle projects therethrough, and said retracting member being movable laterally across said needle to engage said needle and bend said needle and pull the latter to a safe position wherein said needle is covered by a portion of said syringe.

3. An improved disposable syringe adapted to be used but once, said syringe comprising:
    (a) a hollow tubular portion for containing a dose of medicament, and a hypodermic needle, said needle being disposed in an operative position projecting from one end of said tubular portion;
    (b) means in said tubular portion for pumping a dose of medicament through said needle; and
    (c) a disk mounted adjacent to said one end of said tubular portion, said disk being movable across said one end of said tubular portion but being secured to said tubular portion so as not to be readily detachable therefrom, said disk being movable from a first position wherein said needle projects through said disk to a second position wherein said disk moves laterally across said needle to engage the projecting needle and bend the latter thereby retracting the needle out of its projecting position to a safe position wherein said needle is completely covered by a portion of the syringe.

4. An improved disposable syringe adapted to be used but once, said syringe comprising:
    (a) a tubular portion for containing a dose of a medicament, and a hypodermic needle, said needle being disposed in an operative position projecting from one end of said tubular portion;
    (b) means in said tubular portion for pumping a dose of medicament through said needle; and
    (c) a retractor member movably mounted on an external surface of said one end of said tubular member, said retractor member being secured to said one end of said tubular member so as not to be readily removable therefrom, said retractor member being movable from a first position wherein said needle projects through said retractor member to a second position wherein said retractor member moves laterally across said needle to engage and bend the projecting needle until said needle is bent to a safe position wherein said needle is covered by said retractor member.

5. The syringe of claim 4, wherein said retractor member is provided with a through passage which is co-axial with said needle when said retractor member is in said first position, the edge of said passage engaging said projecting needle when said retractor member is moved toward said second position.

6. The syringe of claim 5, wherein said retractor member is a disk mounted on said one end of said housing for rotation about an axis which is radially offset from the axis of said needle.

7. The syringe of claim 6, wherein said disk is provided with an internal chamber into which said through passage opens, said chamber providing means for containing the bent needle.

8. An improved disposable syringe adapted to be used but once, said syringe comprising:

(a) a hollow tubular portion for containing a dose of a medicament, and a hypodermic needle, said needle being mounted on and projecting from one end of said tubular portion, and said tubular portion being formed with a lug, said lug being radially offset from said needle;

(b) means in said tubular portion for pumping a dose of medicament through said needle;

(c) a needle retractor disk mounted on said lug, said retractor disk overlying the majority of said one end of said tubular portion and having a through passage which is co-axial with said needle and through which said needle projects, and said retractor disk being rotatable about said lug whereby said through passage is moved out of alignment with said needle to move said retractor disk against the protruding needle to bend the latter and draw the needle back through said retractor disk through passage to a safe position wherein the bent needle underlies said retractor disk.

* * * * *